United States Patent [19]
Foster et al.

[11] Patent Number: 5,290,249
[45] Date of Patent: Mar. 1, 1994

[54] SURGICAL ACCESS SHEATH

[75] Inventors: Thomas L. Foster, Poland; John S. Lyttle, Spencer; Edward D. Pingleton; Paul G. Thomson, both of Fillmore, all of Ind.

[73] Assignee: Vance Products Incorporated, Spencer, Ind.

[21] Appl. No.: 947,095

[22] Filed: Sep. 17, 1992

Related U.S. Application Data

[63] Continuation of Ser. No. 594,319, Oct. 9, 1990, abandoned.

[51] Int. Cl.$^5$ ............................................. A61B 17/34
[52] U.S. Cl. ................................... 604/174; 604/167
[58] Field of Search .............. 606/198, 167, 184, 171; 604/104, 106, 264, 96, 98, 99, 105, 107, 164, 165, 198, 192, 153, 157, 105, 107, 174, 177

[56] References Cited

U.S. PATENT DOCUMENTS

| | | | |
|---|---|---|---|
| 2,616,429 | 11/1952 | Meren et al. | 604/105 |
| 3,241,554 | 3/1966 | Coanda | 128/350 |
| 3,692,029 | 9/1972 | Adair | 604/105 |
| 3,799,172 | 3/1974 | Szpur | 604/105 |
| 3,946,741 | 3/1976 | Adair | 128/347 |
| 4,043,338 | 8/1977 | Homm et al. | 128/260 |
| 4,069,826 | 1/1978 | Sessions et al. | 604/105 |
| 4,320,762 | 3/1982 | Bentov | 606/198 |
| 4,581,019 | 4/1986 | Curelarn et al. | 604/280 |
| 4,593,681 | 6/1986 | Soni | 128/4 |
| 4,607,620 | 8/1986 | Storz | 128/4 |
| 4,608,965 | 9/1986 | Anspach, Jr. et al. | 128/4 |
| 4,627,838 | 12/1986 | Cross et al. | 604/105 |
| 4,646,722 | 3/1987 | Silverstein et al. | 128/4 |
| 4,654,030 | 3/1987 | Moll et al. | 604/165 |
| 4,808,163 | 2/1989 | Laub | 604/105 |
| 4,848,344 | 7/1989 | Sos et al. | 604/96 |
| 4,995,868 | 2/1991 | Brazier | 604/105 |
| 5,122,122 | 6/1992 | Allgood | 604/167 |

FOREIGN PATENT DOCUMENTS

| | | | |
|---|---|---|---|
| 0432363 | 6/1991 | European Pat. Off. | A61B 17/34 |
| 468805 | 3/1953 | Italy | 604/107 |
| 545347 | 2/1977 | U.S.S.R. | 604/105 |

*Primary Examiner*—John D. Yasko
*Assistant Examiner*—Manuel Mendez
*Attorney, Agent, or Firm*—Richard J. Godlewski

[57] ABSTRACT

A surgical trocar access sheath having a laterally expandable retention mechanism for percutaneous insertion through a body cavity wall. The expandable retention mechanism is positioned about the distal end of the sheath for retaining the access sheath within the body cavity. The access sheath has an inner elongated member cannula and an outer elongated member tube having a slick surface for ready insertion through a puncture site. The laterally expandable retention mechanism includes a plurality of strips extending and formed longitudinally in the outer tube. The retention mechanism has an expanded state and a retracted state. In the expanded state, the longitudinal strips extend radially from the outer elongated member tube to engage the interior surface of the body cavity wall. The expandable retention mechanism is actuated by sliding an actuating mechanism hub attached to the distal end of the outer elongated member tube against another hub fixedly attached to the inner elongated member cannula. To insert or retract the access sheath through the cavity wall of a patient, the physician squeezes the actuating mechanism hub against the fixed hub to collapse the longitudinal strips against the surface of the inner elongated member cannula. Once inserted, the actuating mechanism is released to expand the retention mechanism.

20 Claims, 2 Drawing Sheets

SURGICAL ACCESS SHEATH

This is a continuation of copending application Ser. No. 07/594,319 filed on Oct. 9, 1990 and now abandoned.

TECHNICAL FIELD

This invention relates to surgical trocar access sheaths and, in particular, surgical trocar access sheaths for performing minimally invasive surgical procedures such as endoscopic or laparoscopic surgical procedures.

BACKGROUND OF THE INVENTION

A number of trocar access sheaths are presently available for puncturing the abdominal wall and inserting the sheath into an insufflated body cavity such as the peritoneal cavity. After insertion into the insufflated cavity, the trocar is removed from the passageway of the access sheath and an insufflation line connected to a side port extending laterally from a hub attached to the proximal end of the sheath. An endoscope is commonly inserted through the sheath to provide viewing of the insufflated peritoneal cavity. Additional access sheaths are placed through the abdominal wall to provide further access for other endoscopic surgical instruments. During the surgical procedure, the penetration and position of the endoscope is typically adjusted within the cavity to provide different viewing angles. Various endoscopic surgical instruments are inserted through other access sheaths to manipulate the organs and tissue within the cavity. During the surgical procedure, these endoscopic surgical instruments are often inserted and removed many times from the peritoneal cavity through the access sheaths. During insertion and removal, the access sheaths are inadvertently forced further into the cavity or pulled through the puncture site. A problem with inadvertent removal is the subsequent reinsertion of the sheath into the body cavity through the puncture site. In addition, insufflating gas commonly escapes through the puncture site. Should a large amount of the insufflating gas escape, the reinsertion of the access sheath with a trocar presents the risk of perforating an organ such as a bowel which contaminates the surgical field along with requiring suturing of the perforated tissue.

Suprapubic bladder catheters and gastrostomy feeding tubes in a related field typically utilize a balloon retention cuff about the proximal end thereof to prevent the tube from being inadvertently removed through the abdominal wall. However, the incorporation of a balloon cuff about the distal end of a trocar access sheath presents additional material which must be inserted through the puncture site. Furthermore, additional space consuming lumens must be incorporated into the access sheath to provide inflation and maintenance of the balloon cuff in an expanded state. These inflation lumens or lines add further bulk to the diameter of the access sheath which is clearly undesirable.

SUMMARY OF THE INVENTION

The foregoing and other problems are solved and a technical advance is achieved by an illustrative endoscopic surgical trocar access sheath having a laterally expandable retention mechanism for expanding in a body cavity of a patient after insertion therein. An actuating mechanism attached about the proximal end of the access sheath actuates and maintains the retention mechanism in an expanded state throughout the entire endoscopic surgical procedure. The access sheath includes a rigid inner elongated member cannula with an outer elongated member tube positioned therearound for insertion through the body cavity wall. The outer tube includes a plurality of longitudinally positioned strips formed in the wall of the outer tube that expand and engage the interior surface of the body cavity wall. The actuating mechanism actuates and maintains the plurality of strips in the expanded state.

A proximal hub is attached to the proximal end of the inner cannula and is engaged by the actuating mechanism to actuate and maintain the strips in a laterally expanded state. Advantageously, the actuating mechanism is simply pulled by the physician both during the insertion and removal of the sheath to maintain the strips flush against the rigid inner cannula.

With respect to another advantage of the invention, the outer elongated member tube includes a polytetrafluoroethylene material tube with the laterally expandable strips formed longitudinally in the distal end of the tube. This outer tube not only includes the laterally expandable strips but also presents a smooth, slick surface for readily inserting the access sheath through the puncture site.

A retention disk is also positioned about the outer tube to engage the external surface of the abdominal wall. As a result, the abdominal wall is sandwiched between the expanded strips and the retention disk to maintain the surgical access sheath in a relatively fixed position with respect to the abdominal wall. This clearly presents a significant advantage over prior art access sheaths in preventing inadvertent removal from the abdominal body cavity as well as preventing the extension of the sheath into the cavity and the perforation of organs and tissue.

The proximal hub of the access sheath attached about the proximal end of the inner elongated member cannula includes a neck extending distally therefrom and slidably communicating within a chamber of the actuating mechanism. The actuating mechanism includes a distal hub including the chamber longitudinally positioned therein for slidably communicating with the neck of the proximal hub. A spring is positioned about the inner cannula within the chamber of the distal hub to engage a distal end wall of the distal hub and the distal neck end of the proximal hub to maintain the strips in the expanded state. A set-screw projection is advantageously included to extend into the distal hub chamber and into a longitudinal slot formed in the neck of the proximal hub to limit the longitudinal movement of the actuating mechanism with respect to the proximal hub.

The proximal hub includes a flexible seal positioned about the proximal end thereof and having an aperture therein for permitting a trocar rod to be inserted therethrough and into the passageway of the inner elongated member cannula. An end cap is positioned about the proximal end of the trocar rod to permit the surgeon to readily pierce the cavity wall and insert the trocar and access sheath through the puncture site and into the peritoneal cavity of the patient. The proximal hub also advantageously includes a chamber wherein a side port extends laterally from the proximal hub and communicates with the proximal hub chamber. An insufflation line is readily connected to the side port.

A retainer cap is also fixedly positioned at the distal end of the outer and inner elongated members to maintain the relative fixed position of the two distal ends.

The retainer cap is also beveled to further ease entry of the access sheath through the puncture site.

DETAILED DESCRIPTION

Figure 1:
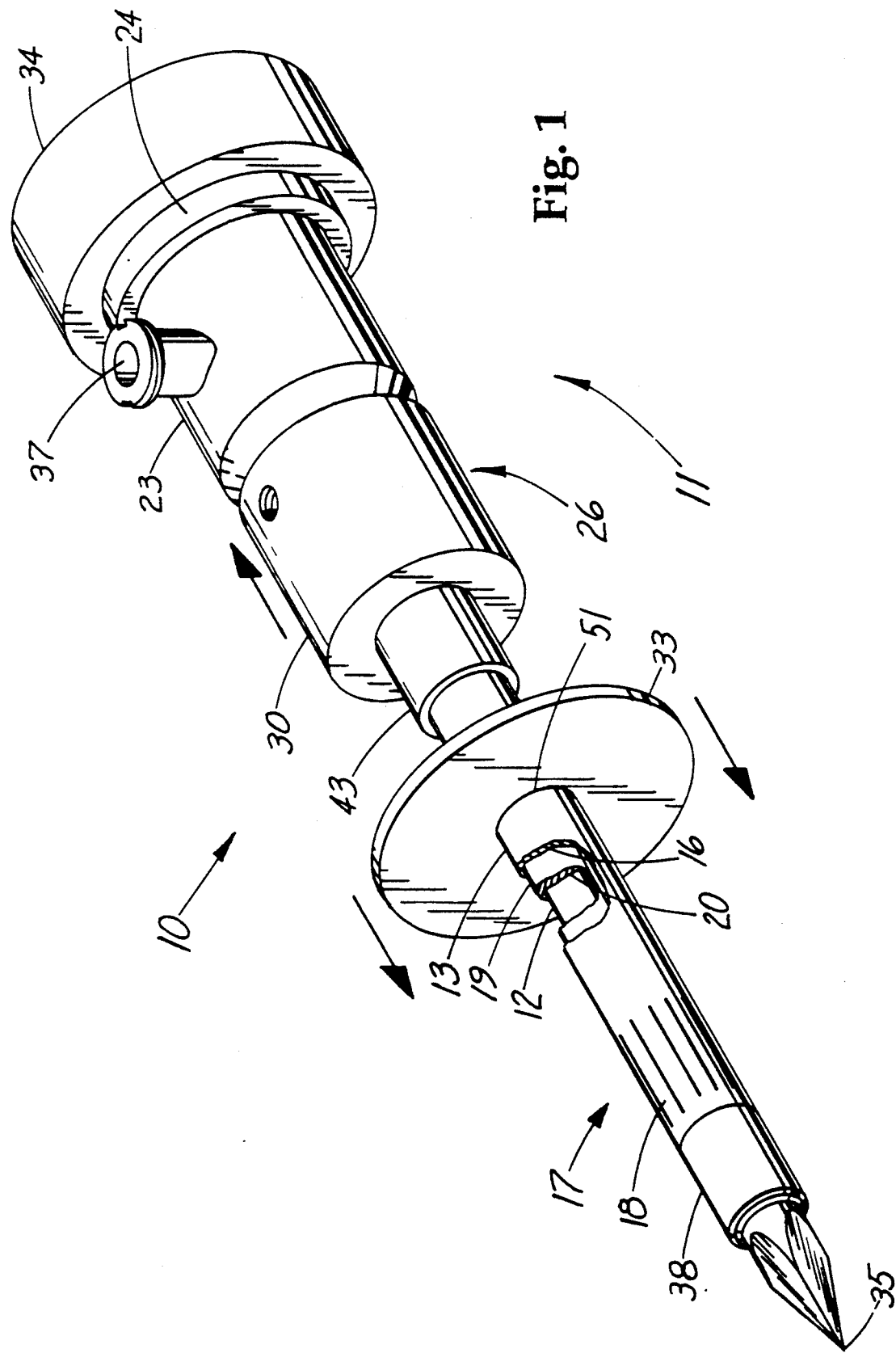
FIG. 1 depicts a preferred illustrative embodiment of the surgical trocar access sheath apparatus of the present invention.

Depicted in FIG. 1 is a preferred illustrative embodiment of surgical trocar access sheath apparatus 10 for percutaneous insertion into a body cavity such as the peritoneal cavity. Surgical apparatus 10 includes access sheath 11 with trocar rod 12 longitudinally extending through the sheath. The trocar rod includes a well-known three-sided pointed distal end 35 for puncturing the abdominal wall and an end cap 34 for pushing the trocar rod and access sheath 11 through the abdominal wall and into the peritoneal cavity. Trocar rod 12 is, for example, 300 series stainless steel approximately 5.6875" in length and 0.195" in diameter. Proximal end 41 of the rod includes a plurality of 8-32 threads for attaching end cap 34 thereto. The distal end of the rod is ground to form three-sided pointed distal end 35. End cap 34 is a cylindrical disk of a high durometer copolymer material approximately 0.625" in height and having a diameter of 1.6". The disk is tapped with 8-32 threads to a depth of 0.4".

Access sheath 11 includes outer elonqated member tube 13 and inner elongated member cannula 19 attached about their distal ends with retainer cap 38. Retainer cap 38 is a stainless steel sleeve approximately 0.260" in length with an outer diameter of 0.269". The retainer cap is compression-fitted in a well-known manner onto the distal end of the inner and outer elongated members.

Positioned about the distal end of the outer elongated member tube is laterally expandable retention mechanism 17 which includes a plurality of strips 18 extending and formed longitudinally in the tube. Retention mechanism 17 has an expanded state and a retracted state. As shown in FIG. 1, the retention mechanism is in the retracted state with longitudinal strips 18 collapsed against inner elongated member cannula 19. With the retention mechanism in the retracted state, the trocar and access sheath are in a position ready for insertion through the abdominal wall and into the body cavity. After the distal end of the access sheath is inserted into the body cavity, the retention mechanism assumes the expanded state with longitudinal strips 18 expanding radially outward for retaining the access sheath within the cavity. The trocar is then removed from longitudinally extending passageway 20 of the access sheath.

Surgical apparatus 10 also includes a retention plate or disk 33 having an aperture 51 therethrough for positioning about the outer elongated member tube. The retention disk, which is a commercially available 16 French disk comprised of well-known silicone material, is slidably moveable along the outer tube to the outer surface of the abdominal wall after insertion of the apparatus into the body cavity to prevent inadvertent extension of the access sheath into the cavity. The retention disk and retention mechanism cooperate together to fixedly position the access sheath with respect to the abdominal wall. Upon completion of the surgical procedure, the retention mechanism is collapsed to the retracted state for removal of the access sheath from the body cavity.

Figure 2:
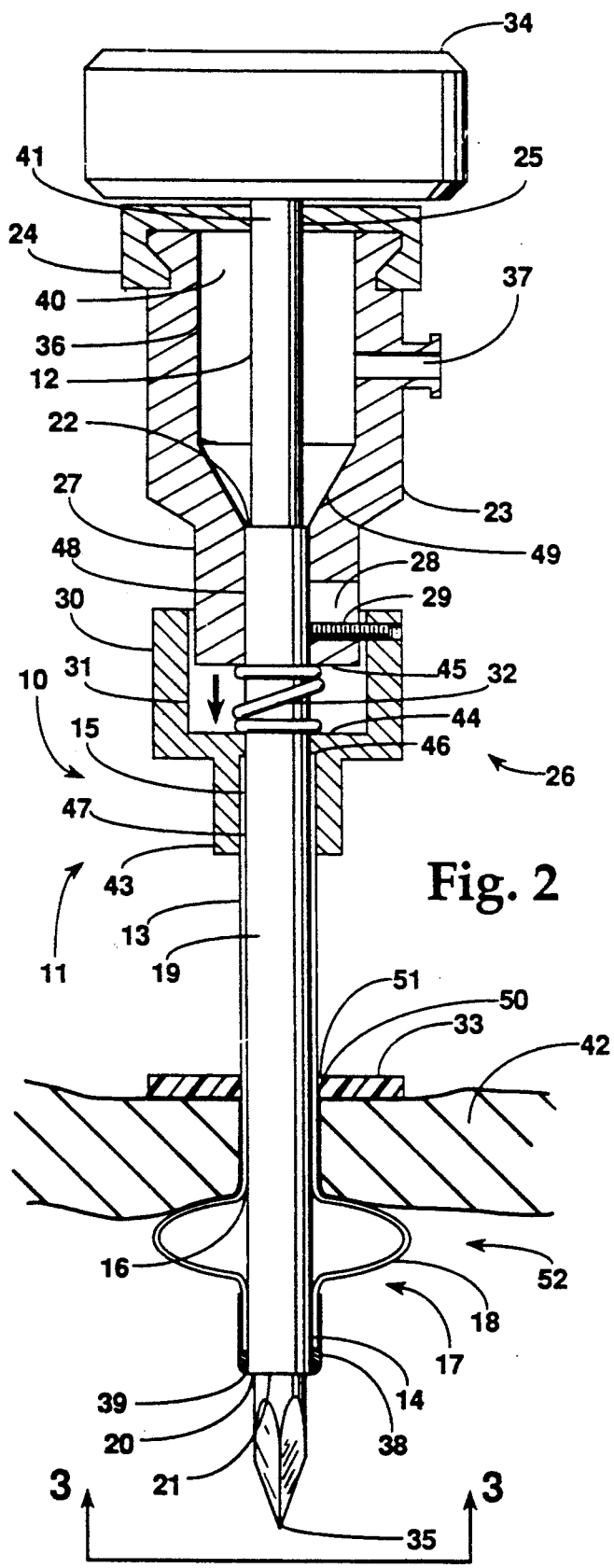
FIG. 2 depicts a partial cross-sectional view of the surgical apparatus of FIG. 1.

Depicted in FIG. 2 is a partial cross-sectional view of surgical trocar access sheath apparatus 10 inserted through abdominal wall 42 and into body cavity 52 via puncture site 50. As shown, retention mechanism 17 is in the expanded state with longitudinal strips 18 extending radially outward to engage the interior surface of the abdominal wall. Retention disk 33 has been slid along outer elongated member tube 13 and engages the outer surface of the abdominal wall. As a result, the distal end of the access sheath is fixedly positioned relative to the abdominal wall.

Figure 3:
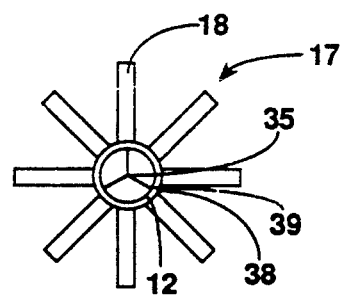
FIG. 3 depicts a front view of the surgical apparatus of FIG. 2 along the line 3—3.

Depicted in FIG. 3 is an end view of retention mechanism 17 along the line 3—3 of FIG. 2. Individual strips 18 extend radially outward from the outer elongated member tube with retainer cap 38 and distal beveled edge 39 showing. Trocar 12 with three-sided pointed distal end 35 is also shown extending from the longitudinal passageway of the inner elongated member cannula.

As depicted in FIGS. 1 and 2, access sheath 11 includes an outer elongated member tube 13 having distal end 14, proximal end 15, and passageway 16 extending longitudinally therethrough. Laterally expandable retention mechanism 17 is positioned about distal end 14 of the outer elongated member tube. The outer elongated member tube is comprised of a commercially available polytetrafluoroethylene polymer material having a slick surface for ready insertion of the tube through the puncture site. For example, outer elongated member tube is a 3.5" length of commercially available thick-wall 18 French polytetrafluoroethylene material tube. Longitudinal strips 18, approximately 0.385" in length, are formed about the distal end of the outer elongated member tube by cutting 8 slits in the outer tube approximately 45 degrees apart.

Positioned within passageway 16 of the outer elongated member tube is inner elongated member cannula 19 having distal end 21 attached about distal end 14 with stainless steel retainer cap 38, proximal end 22, and passageway 20 extending longitudinally between the distal and proximal ends thereof. The inner elongated member is a commercially available stainless steel cannula having, for example, a length of 4.585" with an outer diameter of 0.230" and an inner diameter of 0.201".

The access sheath also includes proximal hub 23 attached about the proximal end of the inner elongated member cannula. Also included is actuating mechanism 26 positioned distally in relation to proximal hub 23 and attached about the proximal end of the outer elongated member tube, which engages proximal hub 23 for actuating retention mechanism 17 laterally and longitudinal strips 18 radially to the expanded state. Proximal hub 23 is comprised of a commercially available polycarbonate polymer material molded to, for example, a length of approximately 1.435" and an outside diameter of 0.880". The proximal hub includes cylindrical chamber 36 approximately 0.368" in diameter with a beveled surface portion 49 narrowing to a 0.232" diameter and longitudinally extending passageway 48. Proximal end 22 of the inner elongated member cannula is secured in passageway 48 in a well-known manner. Proximal end 40 of the hub and chamber includes a flanged portion for attaching flexible seal 24 thereto. The flexible seal has an aperture 25 for extending the trocar therethrough and into chamber 36. The seal is comprised of, for example, silicone material and forms a gas-tight seal about the trocar when positioned therethrough. Extending laterally from the hub chamber is access port 37 having a well-known female Luer-lock connector for attaching an insufflation gas line thereto. The proximal end of the hub narrows to form cylindrical neck 27 which is approximately 0.240" in length and includes passageway 48 for receiving and securing proximal end 22 of the inner elongated member cannula. Slot 28, approximately 0.155" in length, extends longitudinally in the neck for receiving projection 29 such as a 4-40×0.250" set-screw for limiting the travel of actuating mechanism 26 with respect to proximal hub neck 27.

Actuating mechanism 26 includes distal hub 30 attached about proximal end 15 of outer elongated member tube 13 and spring 32 positioned about proximal end 22 of inner elongated member cannula 19 within chamber 31 of the distal hub. The distal hub is also comprised of a commercially available polycarbonate polymer material molded with an outside diameter of, for example, 0.870" with chamber 31 extending longitudinally therein for approximately 0.665" and having a diameter of 0.470". The chamber is open ended at the proximal end of the hub and has end wall 44 at the distal end of the hub. Spring 32 positioned about the cannula engages distal end 45 of neck 27 of the proximal hub and distal end wall 44 to push the two hubs apart and actuate retention mechanism 17 to the expanded state. Projection 29, such as a well-known set-screw, extends radially into chamber 31 and longitudinal slot 28 of neck 27 to limit the longitudinal travel of the distal hub with respect to the proximal hub. The distal end of actuating mechanism hub 30 reduces to cylindrical neck 43 having an outside diameter of approximately 0.380" and a length of 0.390". Neck 43 has longitudinal passageway 47 therein for receiving and attaching to proximal end 15 of the outer elongated member tube using, for example, commercially available medical grade adhesive. Shoulder 46 at the proximal end of the neck passageway limits the insertion of the outer elongated member tube within the passageway. Inner elongated member cannula slidably passes through an aperture in shoulder 46 of distal end chamber wall 44 and into the passageway of the outer elongated member tube.

In summary, actuating mechanism 26 of the access sheath maintains retention mechanism 17 in the expanded state with, for example, longitudinal strips 18 laterally expanded to retain the distal end of the sheath against the interior surface of the patient's abdominal wall. To insert or retract the access sheath through the abdominal wall of the patient, the physician grasps the actuating mechanism and squeezes moveable distal hub 30 of the actuating mechanism against fixed proximal hub 23 to collapse longitudinal strips 18 against the surface of the inner elongated member cannula.

It is to be understood that the above-described surgical trocar access sheath apparatus for percutaneous access of a body cavity is merely an illustrative embodiment of the principles of this invention and that other apparatus may be devised by others skilled in the art without departing from the spirit and scope of this invention. In particular, the retention mechanism may be comprised of other radially expandable devices such as wires and other longitudinally flexible means for radially expanding and engaging the interior surface of the abdominal wall. It is contemplated that the actuating mechanism may also be comprised of other engaging mechanisms for longitudinally sliding the inner and outer elongated members with respect to each other. Helical corkscrew arrangements for the actuating mechanisms are also contemplated.

What is claimed is:

1. A surgical access sheath comprising:
   a first elongated member having a slick outer surface, a first distal end, a first proximal end, a first passageway extending longitudinally between said first ends, and a retention mechanism positioned about said first distal end and having a predetermined state;
   a second elongated member positioned within said first passageway and having a second distal end attached about said first distal end, a second proximal end, and a second passageway extending longitudinally between said second ends, said retention mechanism assuming said predetermined state when said first and second proximal ends are urged longitudinally apart;
   a proximal hub attached about said second proximal end of said second elongated member and having a longitudinal slot therein; and
   a distal hub separate from said proximal hub, attached about said first proximal end of said first member, and having a projection extending therefrom and into said longitudinal slot of said proximal hub; and
   spring means positioned between and contacting said proximal hub and said distal hub for urging said distal and proximal hubs longitudinally apart.

2. The access sheath of claim 1 wherein said retention mechanism includes a plurality of strips longitudinally positioned about said first distal end of said first elongated member.

3. The access sheath of claim 1 wherein said first member includes a tube and said retention mechanism includes a plurality of strips formed longitudinally in said tube about said first distal end.

4. The access sheath claim 1 wherein said first elongated member comprises a polytetrafluoroethylene material tube and said retention mechanism includes a plurality of strips formed longitudinally in said tube about said first distal end.

5. The access sheath of claim 1 further comprising a retention plate extending laterally from said first member and slidably engaging said first member.

6. The access sheath of claim 1 wherein said proximal hub includes a chamber and a side port extending laterally therefrom and communicating with said chamber.

7. The access sheath of claim 6 further comprising a seal positioned about a proximal end of said proximal hub and having an aperture therein communicating with said chamber.

8. The access sheath of claim 1 wherein said proximal hub includes a neck extending distally and wherein said distal hub has a chamber longitudinally positioned therein, said neck communicating with said chamber.

9. The access sheath of claim 8 wherein said spring is positioned within said chamber and engages said neck and said distal hub.

10. The access sheath of claim 9 wherein said neck includes said slot longitudinally positioned therein and wherein said projection extends into said chamber and said slot.

11. The access sheath of claim 1 further comprising a rod sized for extending through said second passageway of said second elongated member.

12. The access sheath of claim 11 wherein said rod includes a predetermined distal end shaped for puncturing a cavity wall of a patient.

13. The access sheath of claim 12 wherein said rod includes an end cap positioned about a proximal end thereof for pushing said access sheath through said cavity wall of said patient.

14. The access sheath of claim 1 further comprising a retainer cap attached to said first and second members about said distal ends thereof.

15. The access sheath of claim 14 wherein said retainer cap includes a beveled distal end.

16. A surgical access sheath comprising
   a pliable material tube having a slick outer surface, a first distal end, a first proximal end, and a first passageway extending longitudinally between said first ends, said tube having a plurality of strips formed longitudinally therein about said first distal end and laterally expandable to an expanded state;
   a rigid cannula positioned within said first passageway of said tube and having a second distal end attached about said first distal end of said first tube, a second proximal end, and a second passageway extending longitudinally between said second ends, said strips assuming said expanded state when said first and second proximal ends are urged longitudinally apart from each other;
   a proximal hub attached about said second proximal end of said cannula and having a longitudinal slot therein;
   a distal hub separate from said proximal hub, attached about said first proximal end of said tube, and having a projection extending therefrom and into said longitudinal slot of said proximal hub; and
   spring means positioned between and contacting said proximal hub and said distal hub for urging said distal and proximal hubs longitudinally apart.

17. The surgical access sheath of claim 16 wherein said proximal hub includes a neck extending distally about said second proximal end of said cannula and wherein said distal hub has a chamber, said neck communicating with said chamber.

18. The access sheath of claim 17 wherein said spring means is positioned within said chamber and about said cannula and engages said neck and said second hub.

19. The access sheath of claim 18 wherein said neck includes a slot longitudinally positioned therein and wherein said distal hub further comprises a projection extending therefrom into said chamber and said slot.

20. A surgical access sheath comprising:
   a flexible polytetrafluoroethylene material tube having a slick outer surface, a first distal end, a first proximal end, and a first passageway extending longitudinally between said first ends, said tube also having a plurality of strips formed longitudinally therein about said first distal end and laterally expandable to an expanded state;
   a rigid stainless steel cannula positioned in said first passageway of said flexible tube and having a second distal end, a second proximal end, and a second passageway extending longitudinally between said second ends;
   a retainer cap having a beveled distal end and attached to said distal ends of said tube and said cannula;
   a first hub attached about said second proximal end of said cannula and having a first chamber communicating with said second passageway of said cannula, said hub including an access port extending laterally therefrom and communicating with said first chamber, said hub also including a flexible seal attached about a proximal end of said first chamber and having an aperture therein communicating with said first chamber, said first hub further having a neck extending distally about said second proximal end of said cannula, said neck having a slot longitudinally positioned therein;
   a second hub attached about said first proximal end of said tube and positioned about said cannula, said second hub including a second chamber sized for receiving said neck of said first hub;
   spring means positioned within said second chamber and around said cannula and contacting said neck and said second hub for urging said first and second hubs longitudinally apart and actuating said plurality of strips to said expanded state, said second hub further including a projection extending into said second chamber and said slot;
   a trocar rod having a three-sided pointed distal end and an end cap positioned about a proximal end thereof, said rod extending through said aperture in said seal, said first chamber, and said second passageway of said cannula, said cap engaging said flexible seal and said hub for pushing said access sheath through a body cavity wall of a patient; and
   a retention disk positioned around and extending laterally from said tube and slidably moveable along said tube for fixedly positioning said tube and said cannula with respect to said body cavity wall when said plurality of strips in said expanded state internally engage said body cavity wall.

* * * * *